United States Patent
Kunelius et al.

(10) Patent No.: US 12,178,410 B2
(45) Date of Patent: Dec. 31, 2024

(54) LED LIGHT HUB FOR LARYNGOSCOPE

(71) Applicant: MedSource International LLC, Chanhassen, MN (US)

(72) Inventors: David Kunelius, Waconia, MN (US); Benjamin Beniek, Richfield, MN (US); Sikandar Hayat, Sialkot (PK)

(73) Assignee: MedSource International LLC, Chanhassen, MN (US)

( * ) Notice: Subject to any disclaimer, the term of this patent is extended or adjusted under 35 U.S.C. 154(b) by 263 days.

(21) Appl. No.: 17/539,487

(22) Filed: Dec. 1, 2021

(65) Prior Publication Data

US 2023/0165455 A1 Jun. 1, 2023

(51) Int. Cl.
- *A61B 1/267* (2006.01)
- *A61B 1/00* (2006.01)
- *A61B 1/06* (2006.01)

(52) U.S. Cl.
CPC .......... *A61B 1/267* (2013.01); *A61B 1/00066* (2013.01); *A61B 1/0684* (2013.01)

(58) Field of Classification Search
CPC ............................................ A61B 1/267–2676
See application file for complete search history.

(56) References Cited

U.S. PATENT DOCUMENTS

| | | | |
|---|---|---|---|
| 4,273,112 A * | 6/1981 | Heine | A61B 1/00032 600/199 |
| 4,694,822 A * | 9/1987 | Bauman | A61B 1/0669 600/199 |
| 5,542,905 A * | 8/1996 | Nussenbaum | A61B 1/00032 600/185 |
| 6,036,639 A | 3/2000 | Allred, III et al. | |
| 6,277,068 B1 * | 8/2001 | Wojnowicz | A61B 1/267 600/199 |
| 6,626,556 B2 * | 9/2003 | Galli | F21L 4/027 362/205 |
| 8,257,250 B2 | 9/2012 | Tenger et al. | |
| 10,278,571 B2 | 5/2019 | Poormand | |
| 2009/0187078 A1 | 7/2009 | Dunlop | |
| 2010/0191062 A1 | 7/2010 | Kieffer | |
| 2011/0112378 A1 * | 5/2011 | Heine | A61B 1/00034 320/155 |
| 2014/0100428 A1 * | 4/2014 | Vasan | A61B 1/0669 600/199 |

FOREIGN PATENT DOCUMENTS

| | | |
|---|---|---|
| CN | 203597935 U | 5/2014 |
| EP | 3524134 A1 | 8/2019 |
| WO | 96/20634 A1 | 7/1996 |

OTHER PUBLICATIONS

International Search Report and Written Opinion issued for PCT/US2022/051389, dated Apr. 10, 2023.

* cited by examiner

*Primary Examiner* — Eduardo C Robert
*Assistant Examiner* — Michelle C Green
(74) *Attorney, Agent, or Firm* — WESTMAN CHAMPLIN & KOEHLER, P.A.; Amanda M. Prose

(57) ABSTRACT

A handle mounted light hub for a laryngoscope, the light hub comprising a depressible switch, a light source, and an electrical contact, wherein the switch moves the electrical contact into contact with a power source causing current to flow to power the light source and wherein when depressed, the switch exposes the illuminated light source.

17 Claims, 3 Drawing Sheets

SECTION A-A

LED LIGHT HUB FOR LARYNGOSCOPE

BACKGROUND

The present invention relates to a laryngoscope and more specifically to a light hub for a laryngoscope.

Laryngoscopes are intended to illuminate the larynx or vocal cords for visual inspections. One style of the laryngoscope can be inserted into the patient's mouth to hold down the patient's tongue for a clear view of the patient's throat.

The demand for disposable medical supplies has grown, spurred by the increase in geriatric patients and expanded insurance coverage from the Patient Protection and Affordable Care Act in the U.S. Healthcare organizations have turned to disposables as a response to increased pressure from federal, accreditation organizations and other regulatory bodies to prevent patient and staff harms.

The primary reason for creating disposable devices is infection control. When an item is used only once by a caregiver, it cannot transmit infectious agents to subsequent patients.

While an obvious factor in the design of single-use products could be considered cost, given the nature of medical devices, disposable medical devices require a careful balance between performance, cost, reliability, materials, and shelf life.

Currently, disposable-device assembly depends primarily on injection-molded plastic pieces and/or assembly by bonding, gluing, ultrasonic welding or radio-frequency welding. The high production volume of single-use devices calls for an automated assembly in clean rooms to minimize human contact. Unlike reusable devices, which are often sterilized at the healthcare facility, disposable devices are sterilized before leaving a manufacturing site and are thus provided in a ready-to-use state.

The handle of a laryngoscope supports operational components of the laryngoscope such as a battery assembly including a blade contact assembly with a battery assembly including a battery, battery spring and contact spring such that power to a light source on a blade for the laryngoscope can be illuminated with use of the laryngoscope.

SUMMARY

An aspect of the present disclosure relates to a handle mounted light hub for a laryngoscope. The light hub has a depressible switch; a light source; and an electrical contact. The switch moves the electrical contact into contact with a power source causing current to flow to power the light source and wherein when the switch is depressed, the switch exposes the illuminated light source.

The switch comprises a circular ring surrounding the light source positioned in a center of the ring. In one or more embodiments, the switch protrudes upwardly from and extends above a surface wall of the handle. In one or more embodiments, the switch is a spring biased switch for moving the switch to an off position when depressive force from the blade is removed.

The switch protrudes upwardly from a stationary housing of the light hub and wherein the switch is depressible into the housing and wherein the housing further supports a spring below the depressible switch.

The switch is configured to engage with a blade installed on the handle such that switch engages with the blade when the blade depresses the switch.

The light source is an LED light.

The hub is comprised of a hard plastic material.

The power source is housed within the handle of the laryngoscope.

Another aspect of the present disclosure relates to a light hub for a laryngoscope with a housing supporting a depressible switch and light source, both extending upwardly from a handle of the laryngoscope and wherein the switch is depressible for actuating the light source and to expose the light source for illumination when a blade is installed on the laryngoscope.

The depressible switch comprises a contact surface for the blade that encircles the light source positioned within a center opening in the switch such that the switch can be activated by depressing the switch at any point on the contact surface.

The contact surface is a perimeter ring extending upwardly from the handle a first distance and the light source comprises a bulb extending upwardly from the handle a second distance wherein when the contact surface is depressed the first distance is reduced and the second distance remains static such that depressing the switch illuminates and exposes the light source on the handle in an on position.

The first distance and the second distance are substantially the same when the switch is in an off position.

In one or more embodiments, the light hub is provided on a disposable laryngoscope handle.

The housing further comprises a spring and the spring is compressible between the depressible switch and a floor surface of the housing such that the switch is a spring biased switch.

Yet another aspect of the present disclosure relates to a method of actuating a light for a laryngoscope by providing a laryngoscope with a handle mounted light hub comprising a depressible switch, an LED light source, and an electrical contact. Actuating the light source includes installing a blade on the laryngoscope and depressing the switch with a base of the blade to move the electrical contact into connection with a power source held in the handle of the laryngoscope to expose and illuminate the light source.

Depressing the switch comprises compressing a spring between the switch and a housing of the light hub such that the spring biases the depressive force on the switch.

Disposing of laryngoscope is carried out after a single use.

DETAILED DESCRIPTION

A light hub for a laryngoscope is described herein. The light hub can be provided on a handle of the laryngoscope, where the light hub supports the optics and a depressible switch for activating the light source. The light hub is proved on an upper portion of the handle such that when a laryngoscope blade is connected to the handle, use of the blade activates the light by depressing a portion of the light hub for activating illumination of the light and upon release, deactivating the light source. Depressing the light hub also serves to further expose the light source for increased illumination of the area surrounding the installed blade and for illumination during use of the laryngoscope.

The light hub according to one or more embodiments herein is positioned within a neck portion of the handle with an outer facing switch such that connecting of a base of the blade to the handle places the hub and a switch thereof in a location to be activated by the base of the blade. The light hub comprises a circular switch surrounding the light source.

The light hub can be an LED light hub which provides a fiber optic light source for a laryngoscope. Activation of the light source occurs when force is applied to the light hub and for example, more specifically when force is applied to a switch portion of the light hub. This force may be applied by a contact surface of a laryngoscope blade connected to the handle supporting the light hub.

The switch has a contact surface that extends upwardly from the handle on which the light hub is installed. The light source similarly extends upwardly from the handle. When installed and in an "off" state, the contact surface and the light source extend upwardly from the handle a substantially same distance. In one or more embodiments, the contact surface may extend above or below the light source for different models of light hubs. When the switch is depressed by the installed blade, the contact surface is depressed and/or lowered and thus the switch is lowered into the body of the handle and the light source remains stationary such that depressing the switch further exposes the light source for unobstructed illumination and actuation of the light source.

When lowering the switch an electrical contact surface which is an opposing surface of the switch to the blade contact surface is moved into electrical contact with a power source that may also be stored within the body of the handle. The light source may be a battery.

The light hub also supports a spring for biasing the switch. When the force for depressing the switch is removed, the spring returns the switch to its "off" position and breaking the electrical contact between the switch and the power source.

In one or more embodiments, the light hub and handle assembly is disposable and can be a single use device. One or more of the light hub components may be comprised of a hard plastic.

Figure 1:
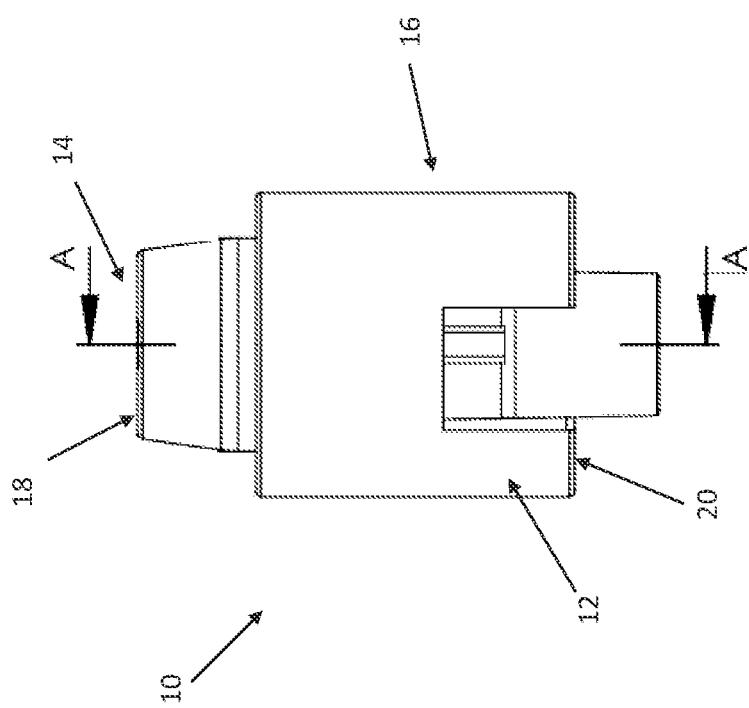
FIG. 1 is a side view of a light hub for a laryngoscope.
Figure 2:
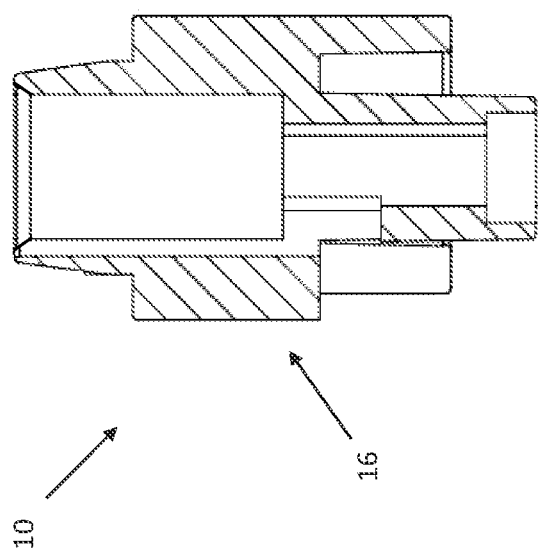
FIG. 2 is a cross-sectional view of the light hub along A-A shown in FIG. 1.

In further detail, in the embodiment illustrated herein, a light hub 10 is illustrated in FIGS. 1-2. The light hub 10 comprises a housing 12 for a light source 14. The light source 14 may be an LED light source. The housing 12 comprises and/or supports a switch assembly 16 which includes a first contact surface 18 which extends upwardly from the housing 12 and surrounds the light source 14 which is also positioned to extend upwardly from the housing 12. The contact surface 18 and the light source are provided and exposable on an upper portion of the light hub 10 so that when installed on a laryngoscope handle 30, the hub 10 and thus switch assembly 16 are accessible from a neck 32 portion of the laryngoscope. When connecting the laryngoscope blade to the neck 32 of the handle 30, a surface on the base of the blade may then physically and directly contact the contact surface 18 of the light hub 10.

Figure 4:
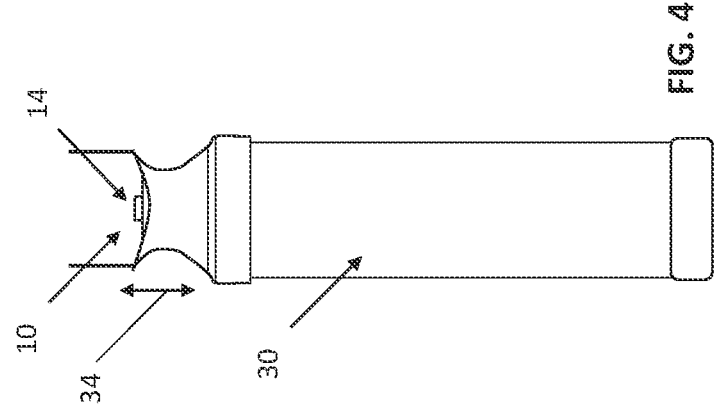
FIG. 4 is a side view of the laryngoscope handle with light hub therein and light source activated.
Figure 3:
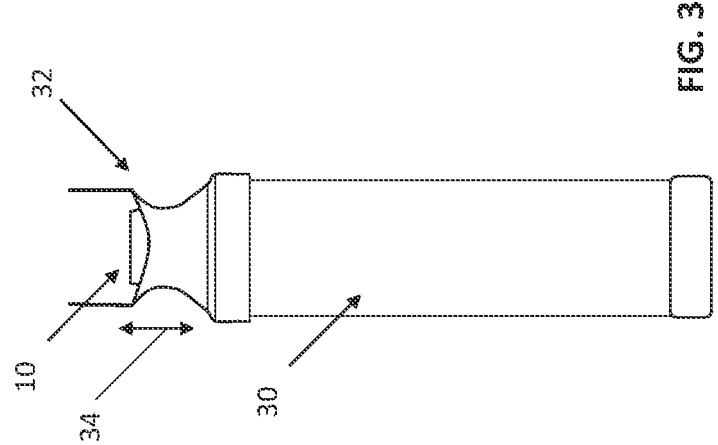
FIG. 3 is a side view of a laryngoscope handle with light hub therein.

Referring to FIGS. 3 and 4, the switch assembly 16 is vertically movable within the housing 12 in reciprocal directions as illustrated by arrows 34. When a force is applied to the contact surface 18, generally a downward force, the switch assembly 16 moves downwardly to contact an opposing surface, a circuit surface 20 of the switch assembly 16 with a power source to illuminate the light source 14. This downward force is generally provided by the blade of the laryngoscope when the blade is installed for use. In FIG. 4, where the switch assembly is moved to activate and expose the light source, the blade is not shown so as to illustrate the position of the switch assembly and light source in the "on" position. However, in embodiments wherein a blade is operably attached to or otherwise supported by the laryngoscope handle, a surface of the blade may directly depress the switch 16 such that the blade itself activates the light source 14. Generally, in this "on" position the blade that is operably connected to the laryngoscope handle is illuminated by the light source which is also positioned to illuminate a field of view around the blade to illuminate an airway in which the laryngoscope is or may be inserted. When the downward force is removed, the switch assembly moves upwardly back to a relaxed position where the light source is deactivated, and the switch is in an "off" position.

The switch assembly 16 may be a spring 22 biased switch assembly wherein the spring provides the force for restoring the switch assembly 16 to an "off" position when the depressive force on the contact surface 18 is removed. In one embodiments, the spring 22 is positioned to be compressed between a floor surface on the housing 12 and the movable switch 16. As the switch 16 is vertically moveable as described above, the switch is lowered and compresses the spring 22 against the floor surface of the housing 12 which is stationary. When downward force to the switch 16 is removed, the spring relaxes and extends to push the switch 16 upwardly and break electrical contact for illumination of the light source 14. Alternatively, the spring may be positioned to be compressed between the switch 16 and an internal surface of the handle 30 when the switch 16 is depressed.

Although the present disclosure has been described with reference to preferred embodiments, workers skilled in the art will recognize that changes may be made in form and detail without departing from the spirit and scope of the disclosure.

The invention claimed is:

1. A handle mounted light hub for a laryngoscope, the light hub comprising:
   a depressible switch;
   a light source; and
   an electrical contact,
   wherein the switch moves the electrical contact into contact with a power source causing current to flow to power the light source and wherein when depressed, the switch exposes the illuminated light source such that the light source is at least partially unobstructed on each side by the switch, the light source being stationary in mounting on a handle of the laryngoscope, and
   wherein the switch is positioned on the handle of the laryngoscope and the switch at least partially surrounding the light source, wherein the switch is configured to engage with a blade installed on the handle of the laryngoscope such that the switch is activated by the blade as the blade depresses the switch to illuminate and expose the stationary light source.

2. The handle mounted light hub of claim 1 wherein the switch comprises a circular ring surrounding the light source positioned in a center of the ring.

3. The handle mounted light hub of claim 2 wherein the switch protrudes upwardly from and extends above a surface wall of the handle.

4. The handle mounted light hub of claim 2 wherein the switch protrudes upwardly from a stationary housing of the light hub and wherein the switch is depressible into the housing and wherein the housing further supports a spring below the depressible switch.

5. The handle mounted light hub of claim 2 wherein the switch is a spring biased switch for moving the switch to an off position when depressive force from the blade is removed.

6. The handle mounted light hub of claim 1 wherein the light source is an LED light.

7. The handle mounted light hub of claim 1 wherein the light hub is comprised of a hard plastic material.

8. The handle mounted light hub of claim 1, wherein the power source is housed within the handle of the laryngoscope.

9. A light hub for a laryngoscope comprising a housing supporting a depressible switch, and light source mounted to the light hub, both extending upwardly from a handle of the laryngoscope,
  wherein the switch is depressible with respect to the housing and light source for actuating the light source and to expose the light source for illumination such that the light source is at least partially unobstructed on each side by the switch when a blade is installed on the laryngoscope, and
  wherein a base of the blade depresses the switch and exposes the light source.

10. The light hub of claim 9 wherein the depressible switch comprises a contact surface for the blade that encircles the light source positioned within a center opening in the switch such that the switch can be activated by depressing the switch at any point on the contact surface.

11. The light hub of claim 10 wherein the contact surface is a perimeter ring extending upwardly from the handle a first distance and the light source comprises a bulb extending upwardly from the handle a second distance wherein when the contact surface is depressed the first distance is reduced and the second distance remains static such that depressing the switch illuminates and exposes the light source on the handle in an on position.

12. The light hub of claim 11 wherein the first distance and the second distance are substantially the same when the switch is in an off position.

13. The light hub of claim 9 wherein the light hub is provided on a disposable laryngoscope handle.

14. The light hub of claim 9 wherein the housing further comprises a spring and the spring is compressible between the depressible switch and a floor surface of the housing such that the switch is a spring biased switch.

15. A method of actuating a light for a laryngoscope comprising:
  providing a laryngoscope with a handle mounted light hub comprising a depressible switch encircling a stationary LED light source, and an electrical contact;
  installing a blade on the laryngoscope;
  depressing the switch with a base of the blade to move the electrical contact into connection with a power source held in the handle of the laryngoscope to expose and illuminate the stationary light source such that the light source is at least
  partially unobstructed on each side by the switch.

16. The method of claim 15 and further comprising disposing of laryngoscope after a single use.

17. The method of claim 15 wherein depressing the switch comprises compressing a spring between the switch and a housing of the light hub such that the spring biases the depressive force on the switch.

* * * * *